(12) United States Patent  (10) Patent No.: US 8,721,661 B2
Mehdizadeh et al.  (45) Date of Patent: May 13, 2014

(54) STRAIN RELIEF APPARATUS FOR USE WITH IMPLANTABLE MEDICAL LEAD

(75) Inventors: Bruce R. Mehdizadeh, Savage, MN (US); Michael J. Kern, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 293 days.

(21) Appl. No.: 13/084,291

(22) Filed: Apr. 11, 2011

(65) Prior Publication Data

US 2011/0257659 A1 Oct. 20, 2011

Related U.S. Application Data

(60) Provisional application No. 61/323,946, filed on Apr. 14, 2010.

(51) Int. Cl.
*A61B 19/00* (2006.01)

(52) U.S. Cl.
USPC .......................................................... 606/130

(58) Field of Classification Search
USPC .......... 600/374, 375, 381, 585; 604/528, 529; 606/129; 607/122, 123, 124, 125, 126, 607/127, 128
See application file for complete search history.

(56) References Cited

U.S. PATENT DOCUMENTS

| 5,843,146 | A | 12/1998 | Cross, Jr. |
| 6,554,802 | B1 | 4/2003 | Pearson et al. |
| 7,591,970 | B2 | 9/2009 | Olson |
| 7,610,102 | B2 | 10/2009 | Kowalczyk |
| 2007/0255320 | A1 | 11/2007 | Inman et al. |
| 2008/0183221 | A1 | 7/2008 | Burdulis |
| 2008/0319419 | A1* | 12/2008 | Kato et al. .................... 604/528 |

* cited by examiner

*Primary Examiner* — Ryan Severson
*Assistant Examiner* — Jonathan W Miles

(57) ABSTRACT

An extensible implantable medical device includes a body defining a lumen extending through the body. The lumen is configured to receive at least a portion of an implantable medical lead. The body includes a non-rectilinearly shaped portion. The non-rectilinearly shaped portion has a first shape spanning a first distance in a relaxed state. The non-rectilinearly shaped portion has a second, more rectilinear, shape spanning a second distance when subjected to a stretching force. The second distance is greater than the first distance. The non-rectilinearly shaped portion returns to the relaxed first shape upon release of the stretching force and is configured to assume the first shape when the lead is inserted into the lumen and no load is placed on the lead or the shaped body portion.

7 Claims, 8 Drawing Sheets

STRAIN RELIEF APPARATUS FOR USE WITH IMPLANTABLE MEDICAL LEAD

The present application claims priority to U.S. Provisional Patent Application No. 61/323,946, filed Apr. 14, 2010, which application is hereby incorporated by reference as if re-written in its entirety.

FIELD

The present disclosure relates generally to accessory devices for use with implantable medical leads; particularly to accessory devices that impart strain relief to implantable medical leads.

BACKGROUND

Implantable medical leads are used in conjunction with electrical medical devices for a variety of purposes, such as delivery of therapy or monitoring of a condition. Implantable medical leads are typically flexible along their length, but are limited in extension by the length of the lead. Due to their limited extensibility, implantable medical leads may be tensioned by movements of the body in which they are implanted. Such tensioning of the lead may cause the lead to limit movement of the patient's body or may cause the lead to migrate or to be pulled from its intended location within the body.

To overcome such problems, extra lead length or slack can be provided to allow for freedom of movement on the part of the patient and little movement of the lead distal portion from or within its intended location. In some cases, loops or coils are introduced in the lead as the lead is being implanted to provide for strain relief. However, as different implanting physicians may form such loops or coils in different manners, the amount and effectiveness of such strain relief may be variable. Further, tissue may adhere to or grow in between extra lead length or slack or loops or coils limiting their effectiveness to provide strain relief.

SUMMARY

This disclosure, among other things, describes an extensible implantable medical device for providing strain relief to at least a portion of an implantable medical lead. The extensible device may be manufactured to specifications that may result in reproducible and reliable strain relief when the extensible device is disposed about at least a portion of a lead. Thus, the strain relief and resulting extensibility of the lead may be readily controlled within reproducible ranges.

In various embodiments, the extensible implantable medical device includes a body defining a lumen extending through the body. The lumen is configured to receive at least the portion of the implantable medical lead. The body includes a non-rectilinearly shaped portion. The non-rectilinearly shaped portion has a first shape spanning a first distance in a relaxed state. The non-rectilinearly shaped portion has a second, more rectilinear, shape spanning a second distance when subjected to a stretching force. The second distance is greater than the first distance. The non-rectilinearly shaped portion returns to the relaxed first shape upon release of the stretching force and is configured to assume the first shape when the lead is inserted into the lumen and no load is placed on the lead or the shaped body portion.

In some embodiments, at least a portion of the body has a radially expandable inner diameter defined by the lumen. The inner diameter of the portion of the body, in a relaxed state, is configured to be less than the outer diameter of the portion of the lead that the lumen is configured to receive. The inner diameter of the portion of the body is configured to be radially expandable to a diameter greater than the outer diameter of the portion of the lead that the lumen is configured to receive to allow insertion of the lead into the lumen. The inner diameter of the portion of the body is biased towards the relaxed state and is configured to grippingly engage the portion of the lead when the lead is inserted into the lumen. Accordingly, longitudinal movement of the lead relative to the extensible device may be prevented or inhibited.

In some embodiments, the extensible device includes an anchor region for retaining the device in tissue when the device is implanted in a patient. The anchor region may include suture holes; barbs; tines; or the like for such purposes. In some cases, the body of the extensible device forms at least a portion of the anchor portion, and the lumen defined by the body extends through the anchor region.

One or more extensible medical devices described herein may be included in kits with one or more leads that the extensible devices are configured to receive and to impart strain relief. The extensible devices may be preloaded on the leads. In some cases, the kits include a tool for facilitating placement of the extensible devices about the lead. The tool may have an elongate member having a distal opening and a lumen extending proximally in the elongate member from the distal opening. The lumen of the elongate member is configured to slidably receive at least a portion of a lead. The lumen of the extensible device is configured to receive the elongate member of the tool. Thus, the extensible device may be placed about the elongate member of the tool, the lead may be inserted in the lumen of the elongate member, and the elongate member may be withdrawn over the lead as the extensible device is maintained in relative longitudinal orientation with the lead to dispose the extensible device about the lead.

In addition to the various advantages described above, other advantages of one or more embodiments of the methods and systems described herein will be apparent to those of skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
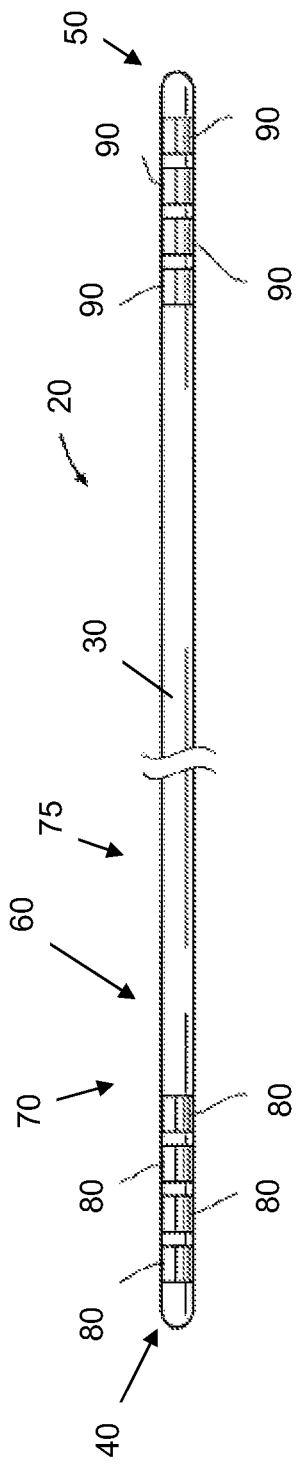
FIGS. 1-2 are schematic plan views of leads.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

As used herein, "implanted", "implantable" or the like with regard to a medical device, means that at least a portion of the device is placed or capable of being placed within a subject, such as a patient. That is, for the purpose of the present disclosure, a device is implanted whether it is fully implanted or partially implanted. For example, a lead may be considered implanted if a distal portion of the lead is placed at a target region in the patient while a proximal portion of the lead is located external to the patient.

This disclosure, among other things, relates to devices, kits, systems and methods that provide strain relief for implantable medical leads. In many embodiments described herein, an accessory device is placed about a lead to provide a reproducible amount of strain relief to the lead. The accessory device is extensible and has a non-rectilinear shape and causes the lead to take on the non-rectilinear shape when the accessory device is placed about the lead. Because the extensible accessory device causes the lead to assume the non-rectilinear shape, the lead and accessory device are extensible when the accessory device is place about the lead.

The accessory devices described herein may be used in conjunction with any suitable implantable medical lead for use with any suitable electrical medical device, such as an electrical signal generator or a monitoring device. Examples of electrical signal generator devices that such leads may be used with include spinal cord stimulators, gastric stimulators, sacral nerve stimulators, deep brain stimulators, cochlear implants, defibrillators, pacemakers, and the like. In many embodiments, such electrical medical devices are implantable.

Figure 2:
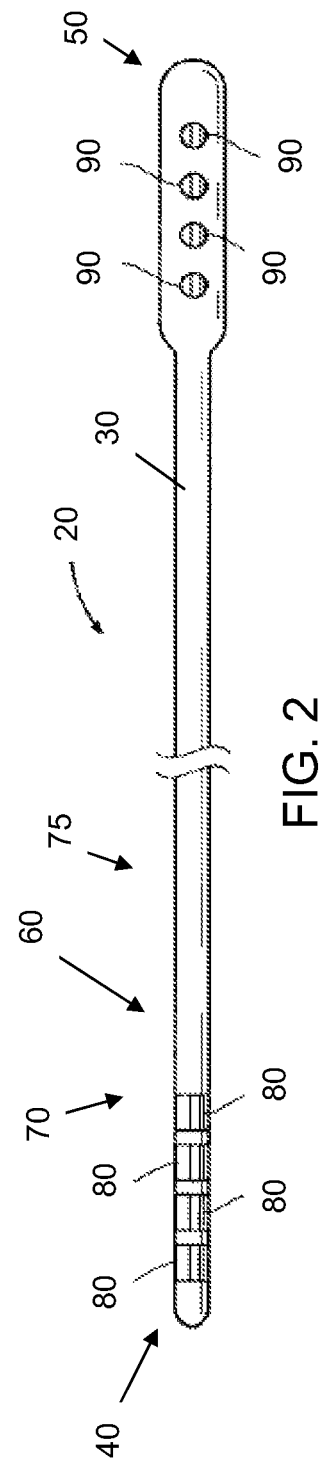

Any suitable type of lead may be employed in accordance with the teachings presented herein. By way of example and with reference to FIG. 1 and FIG. 2, examples of representative leads 20 are shown. Leads 20, as shown in FIGS. 1 and 2, contain four exposed electrical contacts 80 and four electrodes 90. However, leads 20 may contain any suitable number of electrodes 90 or contacts 80. The contacts 80 are disposed in proximity to the proximal end 40 of the lead 20. The electrodes 90 are disposed in proximity to the distal end 50 of the lead 20. Conductive wires (not shown) typically electrically couple discrete contacts 80 with discrete electrodes 90. The conductors run within the lead body 30. The contacts 80 are configured to couple electrical contacts of an active electrical medical device. If the active device is an electrical signal generator, signals generated by the signal generator may be applied to a tissue of a patient in which the distal end 50 of the lead 20 is implanted. That is, a signal generated by the device is transmitted via a contact 80 along a conductor to an electrode 90 and to tissue in which the electrode 90 is in implanted. The lead 20 shown in FIG. 1 is of a type generally referred to as a percutaneous lead. The lead. 20 shown in FIG. 2 is a paddle-type, or surgical, lead. However, it will be understood that any lead configuration may be employed in accordance with the teachings provided herein.

Figure 3:
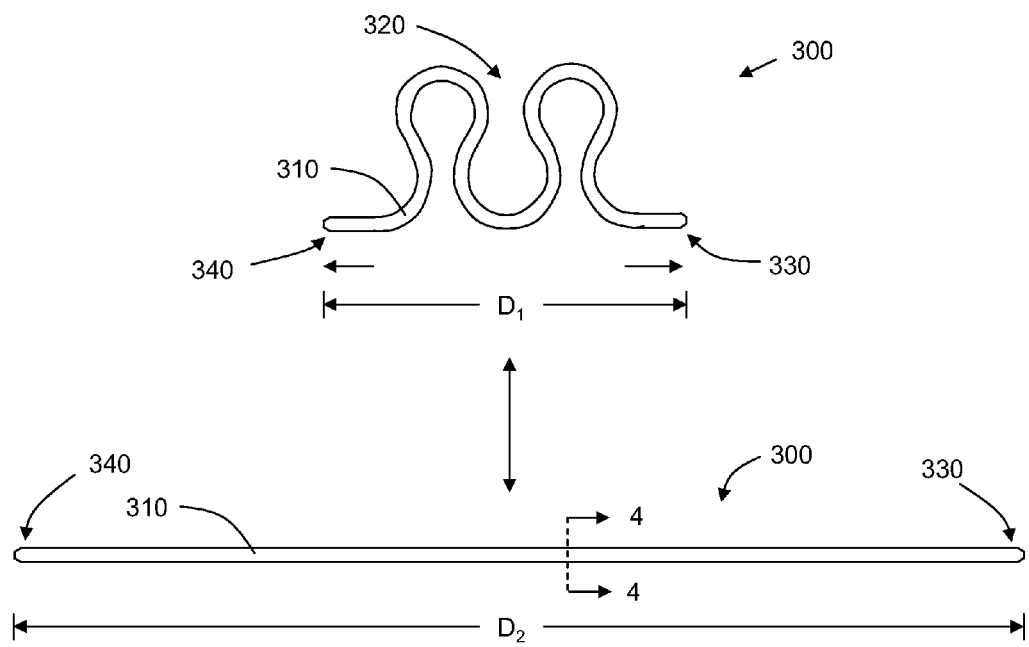
FIG. 3 is a schematic drawing of plan views of an extensible implantable device that may be used to impart strain relief to a lead. The device is shown in a relaxed configuration (top) and an extended configuration (bottom).
Figure 4:
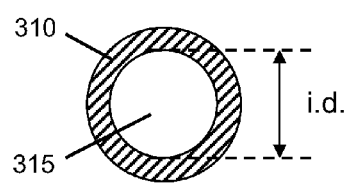
FIG. 4 is a schematic sectional view of the device shown in FIG. 3, taken through line 4-4.

Referring now to FIGS. 3-4, an embodiment of an extensible implantable medical device 300 for imparting strain relief or extensibility to at least a portion of an implantable medical lead is shown. The device 300 includes a body member 310 having a proximal end 330 and a distal end 340 and a lumen 315 (see FIG. 4) extending through the body 310 from the proximal end 330 to the distal end 340. The lumen 315 is configured to slidably receive at least a portion of a lead. The body 310 has an extensible non-rectilinearly shaped portion 320. When the lead is received in the lumen 315, the non-rectilinearly shaped portion 320 causes the lead to assume the non-rectilinear shape of the portion 320.

The non-rectilinearly shaped portion 320 is extensible upon application of a longitudinal stretching force. Upon relaxing of the stretching force, the non-rectilinearly shaped portion 320 returns to its relaxed shape. That is, the non-rectilinearly shaped portion 320, under a no-load condition assumes a desired shape, but the shape is elastically deformable under load and will return to the no-load desired shape once the load is removed. The elastic deformability of the non-rectilinearly shaped portion 320 provides for controlled extensibility under load conditions that may be expected in a particular implanted site, and thus provides predictable and reliable strain relief. In many situations it is desirable to maximize the extensibility of the device while minimizing the load force required to cause extension. However, the non-rectilinearly shaped portion 320 should not so readily deform such that it will not resume its desired shape when a lead is inserted in the lumen 315. Thus, the load force required to cause extension will be balanced against the stiffness of the lead, or portion thereof, to be received in the lumen 315.

While the shaped portion 320 depicted in FIG. 3 is generally sigmoidally shaped (has a repeating sigmoid pattern), it will be understood that any effective shape for providing extensibility is contemplated herein. In many embodiments, the shaped portion 320 includes curved portions rather than sharp bends. The device 300 may include any number of resiliently extensible shaped portions, regardless of shape, for imparting extensibility to a lead. The shaped portions may be formed or created along the length of the device 300 at one or more locations that may be regular or not, or that may extend substantially the entire length of the device 300. While not necessary, it may be desirable for the shaped portion to be symmetrical to provide a balanced extensibility.

The ability to form or set materials for manufacturing the device 300, or portion 320 thereof, into a desired shape or pattern to allow extensibility along at least a portion of the device 300, while allowing the portion to elastically return to the desired shape or pattern under no-load conditions, or conditions in which a lead having a given stiffness is received in the lumen 315 of the device, should be taken into consideration. A combination of construction techniques and material properties can be integrated to create a balanced design providing performance aspects of low load extensibility and desired shaping.

For example, the body 310 of the shaped portion 320 may be formed from one or more layers of polymeric material set to the desired shapes. Examples of suitable polymeric materials that may be employed include silicone, polyurethane, and other soft polymers. Thermal, chemical, or irradiation setting may be employed to set the polymers to achieve the desired shape. The body 310 or portions thereof may be extruded, molded, or the like. By way of example, shaping of a body 310 with thermoset capability can be conducted by bending the body to the desired shape after providing sufficient heat from any heat source or thermal transfer device (based on the material properties) to allow deformable softening of the body 310. Patterns can be created by using mandrels, other shaped surfaces or the like, or a mold can be utilized after or during the heating process that defines the desired pattern. For example, a mold cavity with a repeating sigmoid pattern of sufficient length can be provided and the flexible body member 310 can be routed through the pattern of the mold. Then, a sufficient application of heat can soften and the body to form and set with a newly set memory position based upon the shape or pattern of the mold cavity. Heat can be transferred to the body 310 by way of the mold or otherwise. Cooling to set the pattern can also be provided while within the mold cavity or otherwise as may be permitted under ambient conditions or by heat exchange with a cooling source. Then, with the shaping element(s) set at the desired pattern, elastic deformation of the pattern shape can allow extensibility of the medical device 300.

One or more metallic materials can contribute to the pattern shaping. A variety of metals are easily deformable by applying a bending or shaping force as may be facilitated by shaped surfaces or mold-type cavities. A desirable characteristic of a material includes the ability to be deformed into the desired shape but to do so with the same amount of spring-back force tending to extend the pattern shape. Malleability of the material preferably permits the desired shaping with a spring-back quality. As such, a balance between a spring-back force from one or more metal materials that tend to cause extension with resistance to elastic deformation can be selected to optimize the device 300 performance.

In some embodiments (not shown), a metallic material forms a portion of the body 310 that defines the lumen and a polymeric material is over-molded, coated, or the like, on the metallic material.

Figure 5:
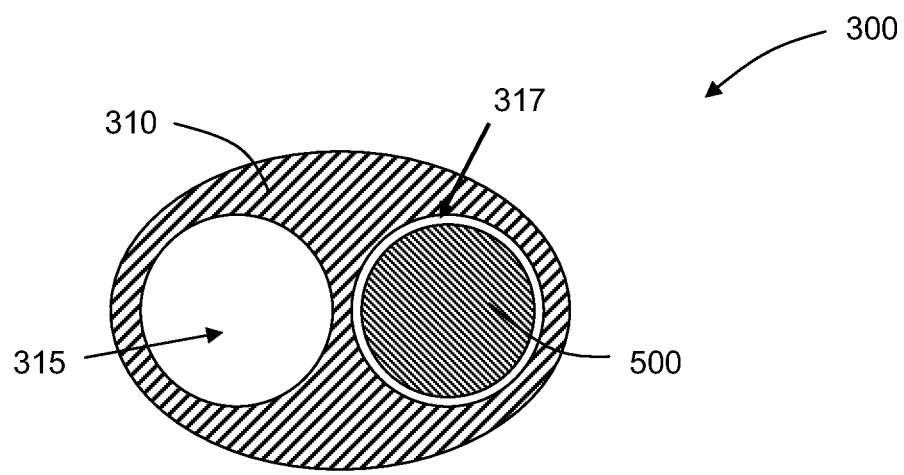
FIG. 5 is a schematic sectional view of an alternative embodiment of the device shown in FIG. 3, taken through line 4-4.

Referring now to FIG. 5, a shaping element 500 may be employed to impart shape to the body member 310 of the device 300. The shaping element 500 may be disposed in a lumen 317 defined by the body member 310, which lumen 317 is adjacent the lumen 315 configured to receive the lead (as depicted), or may be otherwise disposed in body member 310. The shaping element 500 may be solid (as depicted), tubular, or otherwise configured. One or more shaping element 500 may be run along the length of the body 310 any suitable amount to be able to effectively define, or contribute to defining, the desired shape or pattern. The shaping element 500 may be any suitable polymeric, metallic, composite or other material that can impart desired properties of resilient extensibility to the body 310 of the device 300. In some embodiments, the shaping element is a metallic or thermoset polymeric material as described above with regard to the body member. In various embodiments, both the body member 310 and the shaping element 500 are set or formed to impart the desired shape and flexibility to the non-rectilinearly shaped portion 320 of the device 300.

Using the principles described above or those well known in the art, the non-rectilinearly shaped portion 320 may be extensible to any suitable degree. For example and with reference to FIG. 3, in a relaxed state (top) the non-rectilinearly shaped portion 320 spans a first distance (D1), and in a stretched state (bottom) the non-rectilinearly shaped portion 320 spans a second distance (D2). Distance D2 is greater than distance D1 by any suitable amount. For example, D2 may be between 1.5 and 50 times greater than D1; e.g. between 3 and 20 times greater than D1. That is, the non-rectilinearly shaped portion 320 may be stretched to a desired distance (D2) without loosing its ability to elastically return to its relaxed shape that spans a smaller distance (D1).

Figure 6:
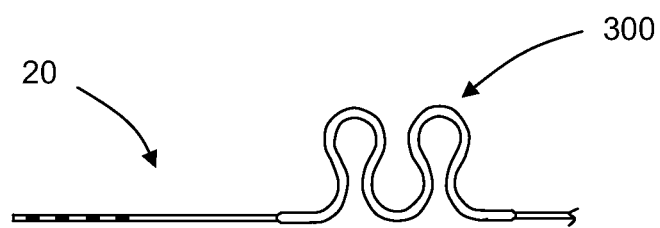
FIG. 6 is a schematic plan view of an extensible medical device disposed about a lead and imparting strain relief to the device.

An example of an extensible device 300 imparting extensibility to at least a portion of an implantable medical lead 20 is shown in FIG. 6. The device 300 is disposed about the lead 20. The portion of the lead 20 disposed in the non-rectilinearly shaped portion of the device 300 assumes the shape of the non-rectilinearly shaped portion of the device 300, and thus is extensible to the extent that the device 300 is extensible. The lead 20 may be inserted into the lumen of the device 300 in any suitable manner. For example, the lead 20 may be fed through the lumen of the device 300 by pushing on the lead 20. If the lead does not have sufficient stiffness to be pushed through the lumen, a stylet (not shown) may be employed, provided that the lead has a lumen for insertion of the stylet, to facilitate insertion of the lead through the lumen of the device. Alternatively, the lead 20 may be attached to a stylet or other pulling member (not shown) that has been fed through the lumen of the device 300, and the lead 20 may be pulled through the lumen of the device 300 via the stylet or other pulling member.

Figure 7:
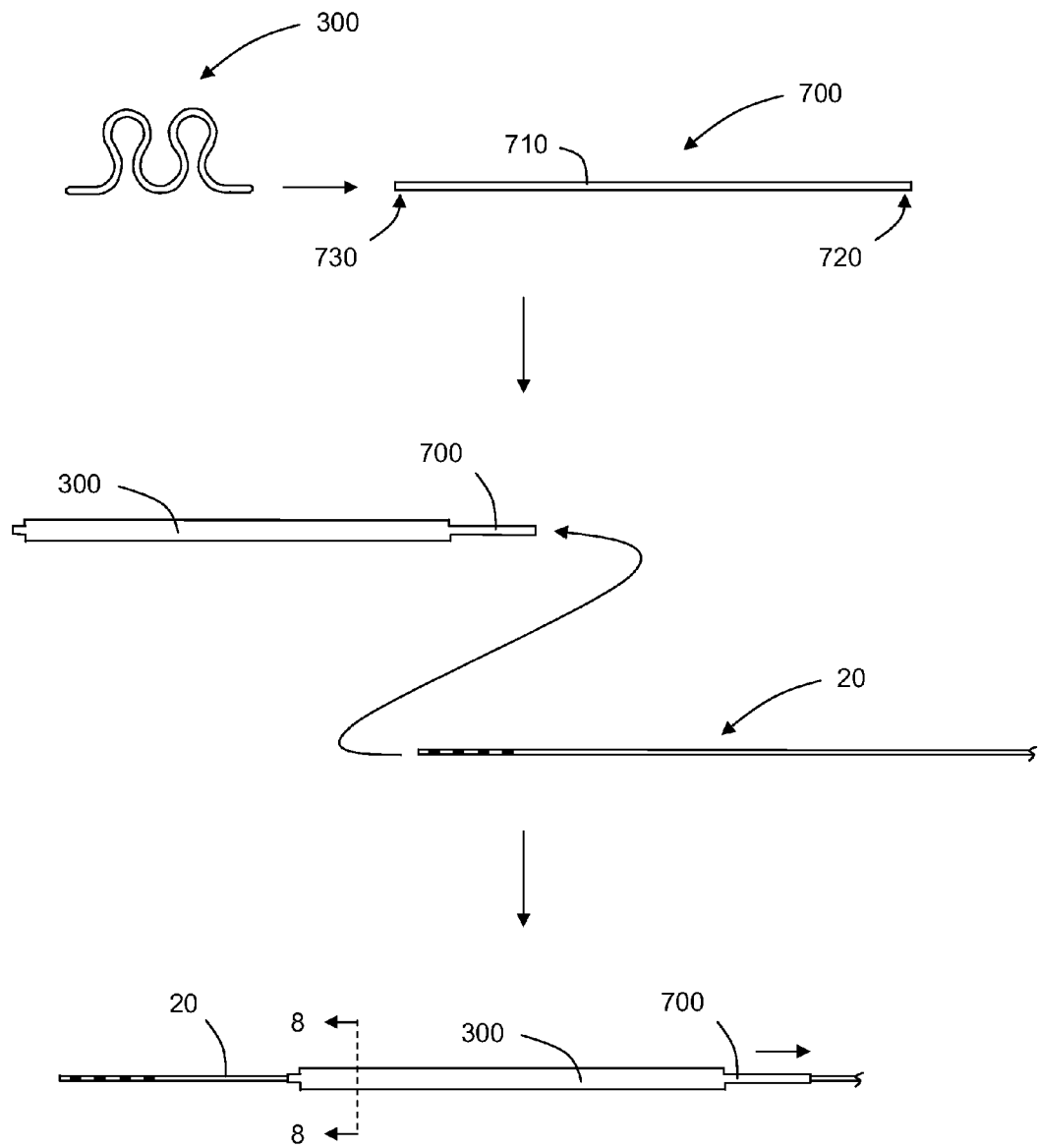
FIG. 7 is a schematic overview of a method for disposing an extensible medical device about a lead using a tool.
Figure 8:
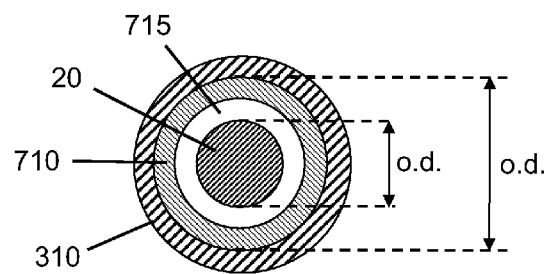
FIG. 8 is a schematic sectional view of an embodiment of the tool, lead, and extensible device depicted in FIG. 7, taken through line 8-8.

In various embodiments, a tool is employed to facilitate insertion of the lead into a lumen of the extensible device. For example and with reference to FIGS. 7-8, the tool 700 may include an elongate body member 710 defining a lumen 715 extending from the proximal end 720 to the distal end 730. The lumen 715 of the tool 700 is configured to slidably receive a lead 20. The lumen 315 (see, e.g., FIGS. 4-5) of the extensible device 300 is configured to receive the elongate member 710 of the tool 700. As shown in the top panel of FIG. 7, the extensible device 300 may be placed about the tool 700 by sliding the elongate member 710 of the tool 700 through the lumen of the extensible device 300. As shown in FIG. 7, the extensible device 300 will extend as the elongate member 710 is slid through the lumen of the device 300 and the non-rectilinearly shaped portion of the device 300 will adopt the shape of the elongate member 710, which in the depicted embodiment is rectilinear. The lead 20 may then be slid through the lumen 715 of the elongate member 710 of the tool 700 (see middle and bottom panels of FIG. 7). Once the lead 20 is slid through the elongate member 710 of the tool 700 such that the extensible device 300 is aligned with a desired portion of the lead 20, the elongate member 710 of the tool 700 may be withdrawn distally over the lead 20, while the extensible device 300 is held in position relative to the lead 20. As the elongate member 710 of the tool 700 is removed and the extensible device 300 is placed about the lead 20 (so that the lead 20 resides in the lumen of the device 300), the extensible device 300 causes the lead 20 to adopt the shape of the device 300 (see, e.g., FIG. 6).

Any suitable tool 700 having any suitable elongate member 710 may be employed in accordance with the teaching resented herein. Typically, the elongate member 710 may be made from rigid metallic or polymeric materials. In various embodiments, a tool as described in U.S. Patent Publication No. 2009/0248054 (published on Oct. 1, 2009, entitled ANCHOR AND ANCHOR DEPLOYMENT APPARATUS, which published patent application is hereby incorporated herein by reference in its entirety to the extent that it does not conflict with the present disclosure) may be used.

The tool 700 may be packaged as a kit with the extensible device 300. The extensible device 300 may be preloaded onto the elongate member 710 of the tool 700 in the kit. The kit may also include one or more leads 20.

Figure 9:
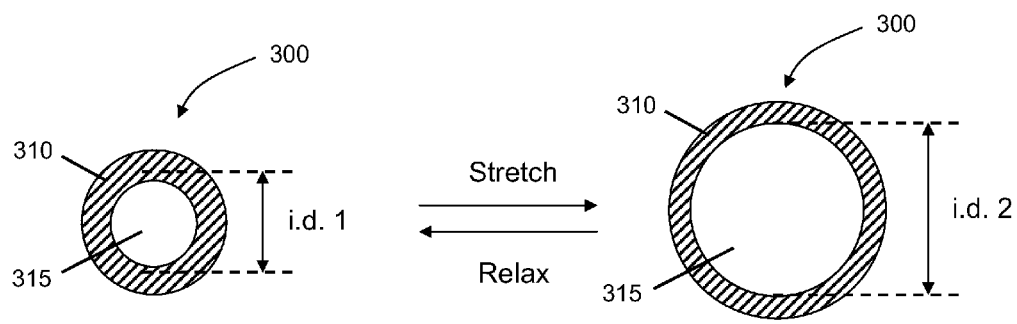
FIG. 9 is a schematic sectional view of an embodiment of a radially expandable extensible medical device is a relaxed state (left) and radially expanded state (right).

In various embodiments and referring to FIG. 9, at least a portion of the body 310 of the extensible device 300 is radially expandable in an elastic manner. In a relaxed state, the inner diameter of at least a portion of the body 310 has a first inner diameter (i.d. 1) defined by the lumen 315. In many embodiments, the first inner diameter (i.d. 1) is less than the diameter of a lead that the lumen 315 of the device 300 is configured to receive. The body 310 is radially expandable to a second inner diameter (i.d. 2) in a stretched state. The second inner diameter (i.d. 2) is greater than the first inner diameter (i.d. 1). The second inner diameter (i.d. 2) may be larger than the outer diameter of the lead to allow the lead to be inserted through the lumen 315. If a tool is to be used, the second outer diameter (i.d. 2) may be larger than the outer diameter of the elongate member 710 (see, e.g., FIG. 8) of the tool. The body 310 is biased toward the first inner diameter (i.d. 1) such that upon release of the radially expanding force, the body 310 may grippingly engage a lead inserted into the lumen 315 and prevent or inhibit longitudinal movement of the device 300 relative to the lead. It will be understood that the principles and description presented in U.S. Patent Publication No. 2009/0248054, published on Oct. 1, 2009, entitled ANCHOR AND ANCHOR DEPLOYMENT APPARATUS, regarding anchors with respect to radial expansion and gripping engagement of a lead may be employed herein with regard to the extensible devices or portions thereof.

Figure 10:
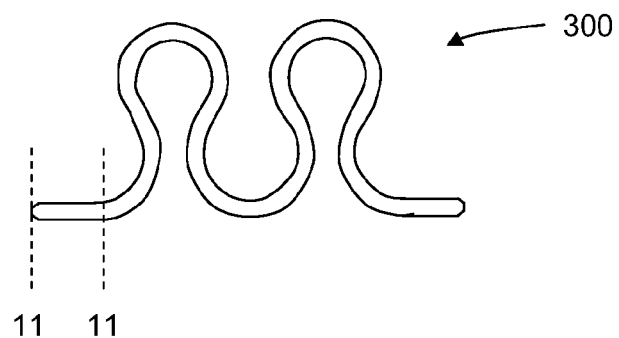
FIG. 10 is a schematic plan view of an embodiment of an extensible medical device that may impart strain relief to an implantable medical lead.
Figure 11:
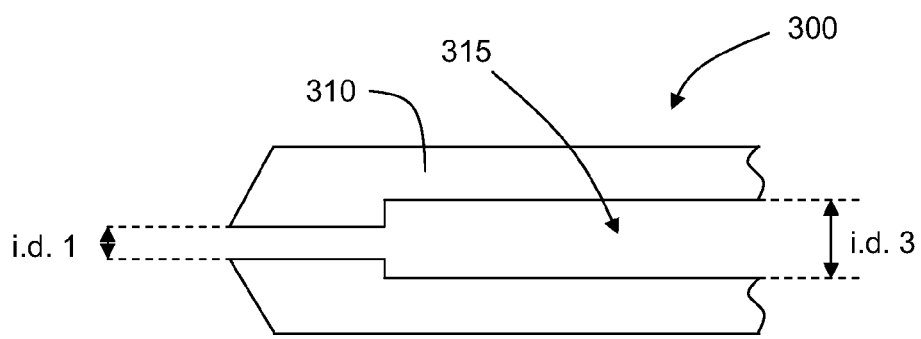
FIG. 11 is a schematic longitudinal sectional view of an embodiment of the device of FIG. 10, between lines 11, 11.

It will be further understood that the lumen 315 of the body 310 may have differing inner diameters along its length and that not all portions of the body member 310 need to grippingly engage a lead (in embodiments where at least a portion of the body member 310 does grippingly engage a lead). For example and with reference to FIGS. 10-12, one or more portions may have inner diameters (i.d. 1) in a relaxed state that are less than a lead that the lumen 315 is configured to receive, and portions may have inner diameters (i.d. 3) that are greater than the outer diameter of the lead configured to be received by the lumen 315. In FIG. 11, an embodiment of the portion of the extensible device 300 shown between lines 11-11 of FIG. 10 is shown. As shown, only a distal portion of the body 310 defines a lumen 315 having an inner diameter (i.d. 1) in a relaxed state that is less than the outer diameter of a lead that may be inserted through the lumen 315. It may be desirable for only a portion of the length of the lumen 315 to have an inner diameter (i.d. 1) in a relaxed state that is less than the outer diameter of a lead that may be inserted through the lumen 315 to facilitate insertion of the lead (or tool if used). The relaxed inner diameter (i.d. 1) and the cumulative length of the lumen 315 defining such an inner diameter can be readily adjusted based on material properties and desired gripping force.

Figure 12:
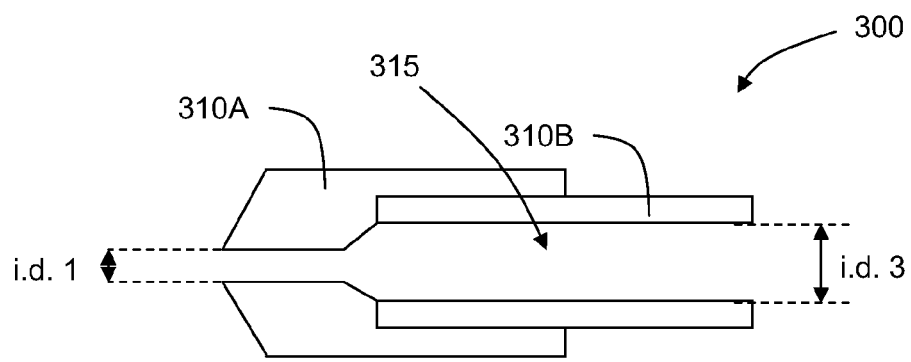
FIG. 12 is a schematic longitudinal sectional view of an alternative embodiment of the device of FIG. 10, between lines 11, 11.

Referring now to FIG. 12, it will be understood that the body 310 or portions thereof of the extensible device 300 may be formed from more than one material. For example, a portion of the body 310B defining a portion of the lumen 315 may be formed of a more rigid, yet extensible material, such as polyurethane, while another portion of the body 310A defining a portion of the lumen 315 may be formed from a softer, more flexible elastic material, such as silicone. The more rigid body portion 310B may impart sufficient stiffness to overcome stiffness of the lead to cause the lead to adopt a non-rectilinear shape of a portion of the device 300, while the more flexible portion of the body 310A may be used for purposes of grippingly engaging the lead. In various embodiments and as depicted, the more flexible portion of the body 310A extends over the more rigid portion 310B of the body and grippingly engages the more rigid portion 310B. Of course the two portions 301A, 310B need not be made of more rigid and more flexible materials and can be operably coupled in any suitable manner; e.g., interference fit, bonded, adhered, welded, joined or otherwise affixed.

Figure 13:
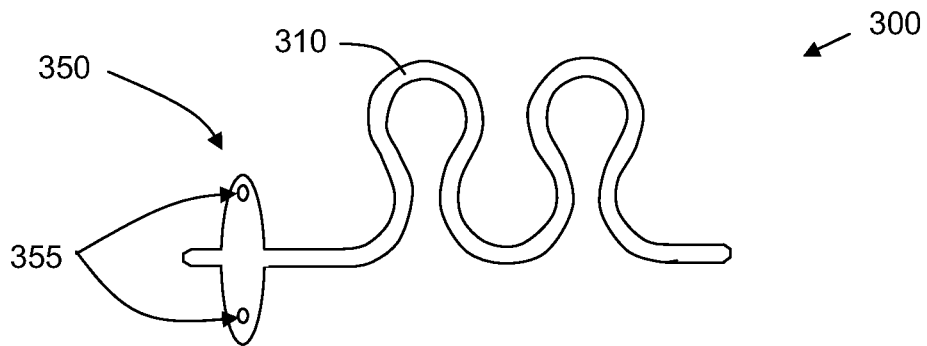
FIG. 13 is a schematic plan view of an embodiment of an extensible implantable medical device having an anchor region.

Referring now to FIG. 13, the extensible device 300 may include a tissue anchoring portion 350. For example, and as depicted, the tissue anchor portion 350 may include one or more holes 355 for suturing the anchor portion 350 to tissue of the patient when the device 300 is implanted. Any suitable anchoring mechanism, such as tines, barbs, suture knobs, or the like, may be incorporated into the extensible device 300. The anchoring portion 350 may be an anchor as described in U.S. Patent Publication No. 2009/0248054, published on Oct. 1, 2009, entitled ANCHOR AND ANCHOR DEPLOYMENT APPARATUS, and may be employed as the portion of the body that grippingly engages a lead (see, e.g., reference number 310A of FIG. 12). An anchor portion 350 may be operably coupled to the body 310 of the extensible device 300 in any suitable manner. For example, the anchor portion 350 may form a part of the body 310 and may define a portion of the lumen through which a lead may be inserted. The body 310 and the anchor portion 350 may be molded or extruded from the same material. The anchor portion 350 may be coupled to the body 310 by interference fit, bonding, adhesive, welding, or may be otherwise affixed or attached to the body 310.

Figure 14:
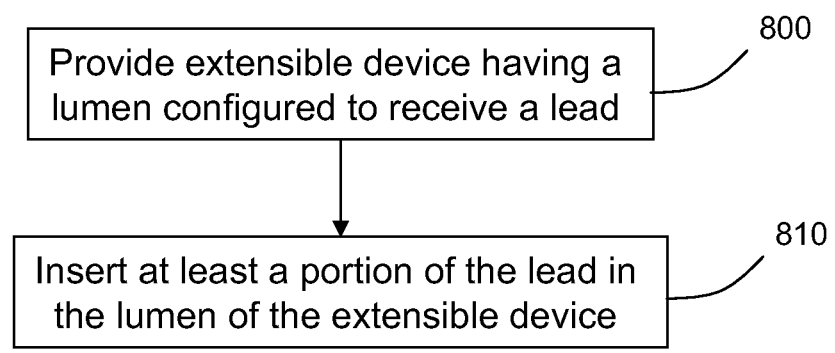
FIGS. 14-15 are flow diagrams illustrating embodiments of methods employing an extensible medical device for imparting strain relief to a lead.
Figure 15:
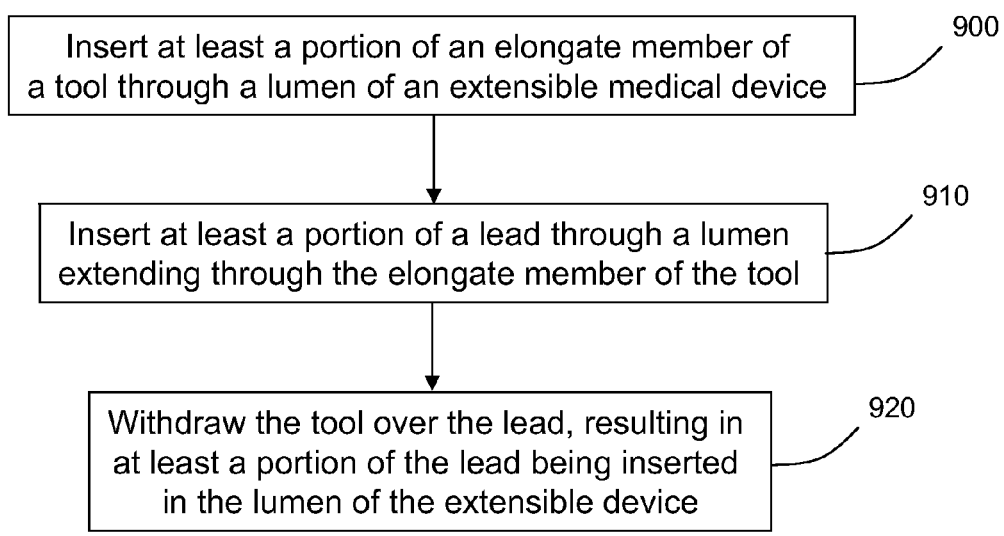

Referring now to FIGS. 14-15, overviews of methods for employing an extensible device as described herein for imparting strain relief to a lead are illustrated. As shown in FIG. 14, a general method for imparting strain relief to a medical lead includes providing an extensible device having a lumen configured to receive a lead (800), e.g. as described herein above, and inserting at least a portion of the lead in the lumen of the extensible device (810).

As illustrated in FIG. 15, a method may include the use of a tool (e.g., as described above with regard to FIGS. 7-8). The method includes inserting at least a portion of an elongate member of a tool through a lumen of an extensible device (900). A lead may inserted through a lumen extending through the elongate member of the tool (910). The tool may then be withdrawn over the lead, as the extensible device is maintained in a longitudinal position relative to the lead, resulting in at least a portion of the lead being inserted in the lumen of the extensible device (920).

Those skilled in the art will recognize that the preferred embodiments may be altered or amended without departing from the true spirit and scope of the disclosure, as defined in the accompanying claims.

What is claimed is:

1. An extensible implantable medical device for providing strain relief to at least a portion of an implantable medical lead, comprising:
    a body defining a lumen extending through the body, wherein the lumen is configured to receive at least the portion of the implantable medical lead, the body having a non-rectilinearly shaped portion,
    wherein the non-rectilinearly shaped portion has a first shape spanning a first distance in a relaxed state,
    wherein the non-rectilinearly shaped portion has a second, more rectilinear, shape spanning a second distance when subjected to a stretching force, the second distance being greater than the first distance,
    wherein the non-rectilinearly shaped portion returns to the relaxed first shape upon release of the stretching force,
    wherein the non-rectilinearly shaped portion is configured to assume the first shape when the lead is inserted into the lumen and no load is placed on the lead or the shaped body portion,
    wherein at least a portion of the body has a radially expandable inner diameter defined by the lumen,
    wherein the inner diameter of the portion of the body, in a relaxed state, is configured to be less than the outer diameter of the portion of the lead that the lumen is configured to receive,
    wherein the inner diameter of the portion of the body is configured to be radially expandable to a diameter greater than the outer diameter of the portion of the lead that the lumen is configured to receive to allow insertion of the lead into the lumen, and
    wherein the inner diameter of the portion of the body is biased towards the relaxed state and is configured to grippingly engage the portion of the lead when the lead is inserted into the lumen.

2. An extensible implantable medical device according to claim 1, wherein the portion of the body that has the radially expandable inner diameter is formed of silicone.

3. An extensible implantable medical device according to claim 1, further comprising an anchor region.

4. An extensible implantable medical device according to claim 3, wherein the body of the extensible medical device forms at least a portion of the anchor region and wherein the lumen formed by the body extends through the anchor region.

5. An extensible implantable medical device according to claim 3, wherein the anchor region comprises a suture hole.

6. A kit comprising:
    an extensible implantable medical device for providing strain relief to at least a portion of an implantable medical lead, the implantable medical device comprising:
    a body defining a lumen extending through the body, wherein the lumen is configured to receive at least a portion of an implantable medical lead, the body having a non-rectilinearly shaped portion,
    wherein the non-rectilinearly shaped portion has a first shape spanning a first distance in a relaxed state,
    wherein the non-rectilinearly shaped portion has a second, more rectilinear, shape spanning a second distance when subjected to a longitudinal stretching force, the second distance being greater than the first distance,
    wherein the non-rectilinearly shaped portion returns to relaxed first shape upon release of the longitudinal stretching force,
        wherein the non-rectilinearly shaped portion is configured to assume the first shape when the lead is inserted into the lumen and no load is placed on the lead or the shaped body portion; wherein at least a portion of the body has a radially expandable inner diameter defined by the lumen,
    wherein the inner diameter of the portion of the body, in a relaxed state, is configured to be less than the outer diameter of the portion of the lead that the lumen is configured to receive,
    wherein the inner diameter of the portion of the body is configured to be radially expandable to a diameter greater than the outer diameter of the portion of the lead that the lumen is configured to receive to allow insertion of the lead into the lumen, and
    wherein the inner diameter of the portion of the body is biased towards the relaxed state and is configured to grippingly engage the portion of the lead when the lead is inserted into the lumen; and
    a tool comprising an elongate member having a distal opening and a lumen extending proximally in the elongate member from the distal opening, wherein the lumen of the elongate member is configured to slidably receive at least a portion of a lead,
    wherein the lumen of the extensible implantable medical device is configured to receive the elongate member of the tool.

7. A kit according to claim 6, wherein the extensible medical device is preloaded on the elongate body member of the tool.

* * * * *